United States Patent [19]

Mongelli et al.

[11] Patent Number: 5,175,182

[45] Date of Patent: Dec. 29, 1992

[54] ACRYLOYL SUBSTITUTED PYRROLE DERIVATIVES

[75] Inventors: Nicola Mongelli, Milan; Giovanni Biasoli, Gavirate; Laura Capolongo; Gabriella Pezzoni, both of Milan, all of Italy

[73] Assignee: Farmitalia Carlo Erba Srl, Milan, Italy

[21] Appl. No.: 613,490

[22] PCT Filed: Mar. 22, 1990

[86] PCT No.: PCT/EP90/00471

§ 371 Date: Nov. 5, 1990

§ 102(e) Date: Nov. 5, 1990

[87] PCT Pub. No.: WO90/11277

PCT Pub. Date: Oct. 4, 1990

[30] Foreign Application Priority Data

Mar. 23, 1989 [GB] United Kingdom ............... 8906709

[51] Int. Cl.$^5$ .................. C07D 277/04; C07D 207/30; C07D 233/54; A61K 31/40; A61K 31/415

[52] U.S. Cl. .................................. 514/428; 544/333; 548/333.5; 548/524; 548/518; 548/194; 548/195; 548/240; 548/245; 548/264.4; 548/314.7; 548/312.7; 514/402; 514/400; 514/371; 514/378; 514/380; 514/383; 514/399; 514/340; 514/341; 514/256; 514/397; 546/275; 546/276

[58] Field of Search ............... 548/518, 524, 353, 342, 548/194, 195, 240, 245, 264.4, 336; 514/428, 402, 400, 371, 378, 380, 383, 399, 400, 340, 341, 256; 546/275, 276; 544/333

[56] References Cited

U.S. PATENT DOCUMENTS

| 557,568 | 5/1938 | Waller et al. | 514/422 |
|---|---|---|---|
| 3,420,844 | 1/1969 | Arcamone et al. | 514/422 |
| 3,420,845 | 1/1969 | Arcamone et al. | 514/422 |
| 3,432,522 | 3/1969 | Preau | 514/422 |
| 4,738,980 | 4/1988 | Arcamone et al. | 514/422 |
| 4,766,142 | 8/1988 | Arcamone et al. | 514/422 |
| 5,017,599 | 5/1991 | Lazzari et al. | 514/422 |

FOREIGN PATENT DOCUMENTS

| 547128 | 10/1957 | Canada | 514/422 |
|---|---|---|---|
| 1421245 | 11/1965 | France . | |
| 1004974 | 3/1964 | United Kingdom . | |
| 1009797 | 8/1964 | United Kingdom . | |
| 1061639 | 7/1965 | United Kingdom . | |

OTHER PUBLICATIONS

P. Chandra et al., "Some Structural Requirements for the Antibiotic ... " Febs Letters, Jan. 1972, vol. 19 #4, pp. 327–330.

Waehnert, U. et al. "Dependent Inactivation of the DNA . . . " Chemical Abstracts, vol. 83 1975 p. 252.

Zimmer, C. et al. "Binding of Analogs of the Antibiotics . . . " Chemical Abstracts, vol. 76, 1972 p. 180.

Nikitin, S. M. "DNA base pair sequence-specific ligands . . . ", Chemical Abstracts, vol. 95, 1981, p. 32; 95:35304r.

Grehn, L. "Synthesis and Antiviral Activity of Dista-
(List continued on next page.)

Primary Examiner—Mary C. Lee
Assistant Examiner—Joseph K. McKane
Attorney, Agent, or Firm—Nikaido, Marmelstein, Murray & Oram

[57] ABSTRACT

The invention relates to acryloyl substituted pyrrole derivatives of formula (I)

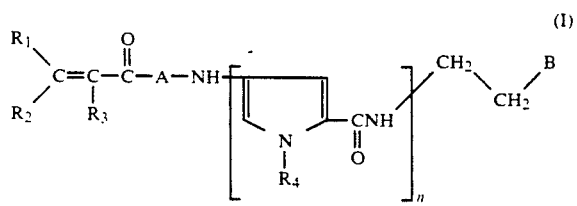

wherein
n is an integer of 1 to 5;
each of $R_1$ and $R_2$, which may be the same or different, is hydrogen, halogen, —CN, —NO$_2$, C$_1$-C$_4$ alkyl, or a group

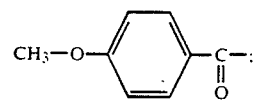

$R_3$ is hydrogen, halogen, —CN, or —NO$_2$;
each $R_4$ is, independently, hydrogen or C$_1$-C$_4$ alkyl;
A is a bond, a group

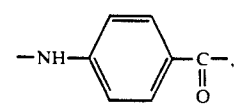

or a group —NH—Het—CO—, wherein Het is a saturated or unsaturated pentatomic or hexatomic heteromonocyclic ring; and B is a group

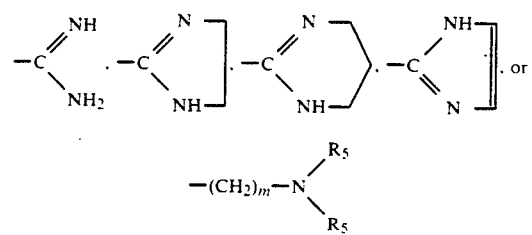

in which m is 1, 2 or 3 and each R$_5$ is, independently, a C$_1$-C$_4$ alkyl group, and pharmaceutically acceptable salts thereof, which are useful as antineoplastic agents.

6 Claims, No Drawings

OTHER PUBLICATIONS mycin A Analogues . . . ", J. Med. Chem, 1983, 26, 1042-1049.

Taylor, J. S. et al. "DNA Affinity Cleaving" Tetrahedron 40, 3, 457 (1984).

Schultz, P. G. et al. "Sequence Specific Double Strand Cleavage of DNA by Bis (EDTA-distamycinFC$^{II}$) and EDTA-Bis(distamycin)Fe$^{II}$", Am. Chem. Soc. 105, 26, 7748 (1983).

Arcamone, F. "On Distamycin and Related Compounds, Selective Antiviral Agents" Med. Chem. 1972, pp. 29-45.

Bialer, M. et al. "Structure-Activity Relationship . . ." Jour. of Med. Chem, 1979, vol. 22, No. 11, pp. 1296-1301.

Chandra, P. et al. "Some Structural Requirements for the Antibiotic Action of Distamycin" FEBS Letters, vol. 16, No. 4, Sep. 1971 pp. 249-252.

Kuroyedov, A. A. et al. "Distamycin A and its Analogs as Agents for Blocking of endo R. EcoRI Activity" Gene, 1 (1977) 389-395.

Arcamone, F. et al. "Structure and Synthesis of Distamycin A" Nature, Sep. 5, 1964 vol. 203, pp. 1064-1065.

Luck, G. et al. "Specific Interactions of Distamycin A . . ." Nucleic Acids Research, vol. 4, No. 8, Aug. 1977, pp. 2655-2671.

Kopka, M. L. et al. "The Molecular Origin of DNA--drug Specificity . . ." Proc. Natl Acad. Sci. USA vol. 82, pp. 1376-1380, Mar. 1985, Biochemistry.

Youngquist, R. S. et al. "Sequence-Specific Recognition . . ." Proc. Natl. Acad. Sci. USA vol. 82 pp. 2565-2569 May 1985. Biochemistry.

Penco, S. et al., "Distamicina A-Nota II . . . " Gazz. Chim. Ital. 97(1967) pp. 1110-1115.

Martinez, J. "Activated N-Nitrosocarbomates for . . ." J. Med. Chem. 1982, 25 pp. 178-182.

ACRYLOYL SUBSTITUTED PYRROLE DERIVATIVES

The invention relates to acryloyl substituted pyrrole derivatives, to a process for their preparation and to pharmaceutical compositions containing them.

The pyrrole derivatives of the invention may be regarded as derivatives of Distamycin A which is a known compound having the following formula

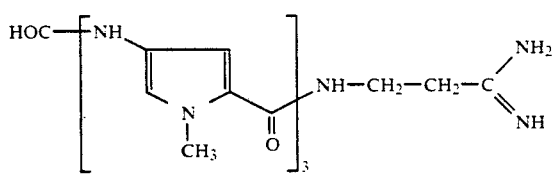

Literature referring to distamycin A includes, for examples Nature 203, 1064 (1964).

The invention provides acryloyl substituted pyrrole derivatives of the following formula (I)

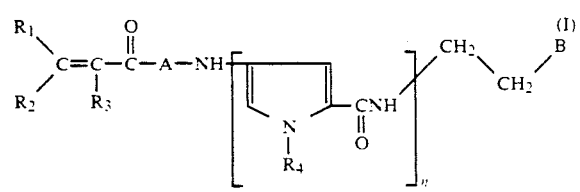

wherein
n is an integer of 1 to 5;
each of $R_1$ and $R_2$, which may be the same or different, is hydrogen, halogen, —CN, —NO$_2$, $C_1$-$C_4$ alkyl, or a group

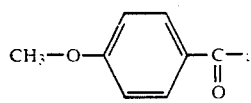

$R_3$ is hydrogen, halogen, —CN, or —NO$_2$;
each $R_4$ is, independently, hydrogen or $C_1$-$C_4$ alkyl;
A is a bond, a group

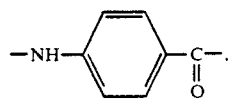

or a group —NH—Het—CO—, wherein Het is a saturated or unsaturated pentatomic or hexatomic heteromonocyclic ring; and
B is a group

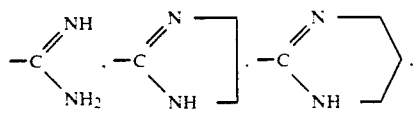

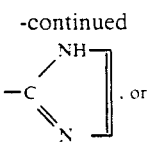

in which m is 1, 2 or 3 and each $R_5$ is, independently, a $C_1$-$C_4$ alkyl group.

The invention includes also the pharmaceutically acceptable salts of the compounds of formula (I) as well as the possible isomers covered by the formula (I), both separately and in mixture. In the above reported formula (I)
n is preferably 3, 4 or 5;
A is preferably a bond or a group

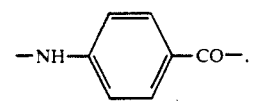

or a group —NH—Het—CO—;
B is preferably a group

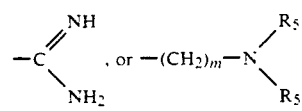

wherein m is preferably 1 and each $R_5$ is methyl.

When A is a group —NH—Het—CO— wherein Het represents a heteromonocyclic ring as defined above, this is, preferably, an unsaturated pentatomic or hexatomic heteromonocyclic ring containing at least one, preferably one or two, heteroatom chosen from O, S and N. Examples of said heteromonocyclics are thiophene, thiazole, pyridine, isoxazole, furane, triazole and imidazole.

When $R_1$ and $R_2$ are the same, they are, preferably, hydrogen.

When $R_1$ and $R_2$ are different, $R_1$ is, preferably, hydrogen and $R_2$ is, preferably, a halogen; the halogen is, preferably, chlorine or bromine.

When $R_3$ is halogen, it is, preferably, chlorine or bromine.

Preferably each group $R_4$, independently, is $C_1$-$C_4$ alkyl, in particular methyl and, most preferably, all groups $R_4$ are methyl.

As already said, the invention includes also the pharmaceutically acceptable salts of the compounds of formula (I).

These salts are the salts with pharmaceutically acceptable acids, either inorganic acids such as e.g., hydrochloric, hydrobromic, nitric and sulfuric, or organic acids such as, e.g., citric, tartaric, maleic, fumaric, methanesulfonic and ethanesulfonic.

A preferred class of compounds under this invention is represented by the compounds of formula (I) wherein n is 3, 4 or 5;
A is a bond or the group

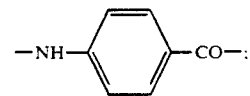

B is a group

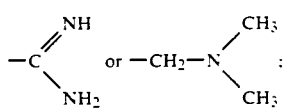

$R_1$ and $R_2$ are hydrogen;
$R_3$ is chlorine or bromine and $R_4$ is methyl,
especially in the form of salts with hydrochloric acid.

Specific examples of preferred compounds under this invention, especially in the form of salts with hydrochloric acid, are the following:

N-deformyl-N-(α-chloroacryloyl) Distamycin A;

β-(N-methyl-4-(N-methyl-4-(N-methyl-4-(N-methyl-4-(α-chloro-acrylamido) pyrrole-2-carboxamido) pyrrole-2-carboxamido) pyrrole-2-carboxamido) pyrrole-2-carboxamido) propionamidine;

N-deformyl-N-(α-bromoacryloyl) Distamycin A;

β-(N-methyl-4-(N-methyl-4-(N-methyl-4-(N-methyl-4-(α-bromoacrylamido) pyrrole-2-carboxamido) pyrrole-2-carboxamido) pyrrole-2-carboxamido) pyrrole-2-carboxamido) propionamidine;

β-(N-methyl-4-(N-methyl-4-(N-methyl-4-(N-methyl-4-(N-methyl-4-(α-bromoacrylamido) pyrrole-2-carboxamido) pyrrole-2-carboxamido) pyrrole-2-carboxamido) pyrrole-2-carboxamido) pyrrole-2-carboxamido) propionamidine;

N-deformyl-N-(4-(α-bromoacrylamido) benzoyl)-Distamycin A;

3-(N-methyl-4-(N-methyl-4-(N-methyl-4-(N-methyl-4-(α-chloroacrylamido) pyrrole-2-carboxamido) pyrrole-2-carboxamido) pyrrole-2-carboxamido) pyrrole-2-carboxamido) propyl-dimethylamine.

The compounds of formula (I) are prepared by a process comprising

A) reacting a compound of formula (II)

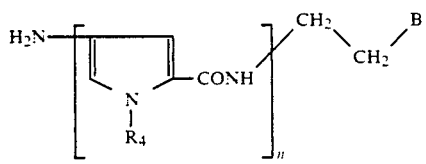

wherein n, $R_4$ and B are as defined above, or a salt thereof, with a compound of formula (III)

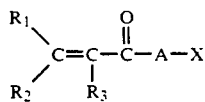

wherein $R_1$, $R_2$, $R_3$ and A are as defined above and X is hydroxy or a leaving group, so obtaining a compound of formula (I) or a salt thereof; or B) reacting a compound of formula (IV)

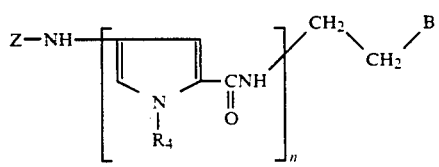

wherein Z is

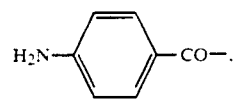

or $H_2N$—Het—CO—, and n, $R_4$, B and Het are as defined above, or a salt thereof, with a compound of formula (V)

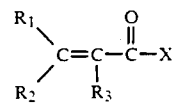

wherein $R_1$, $R_2$, $R_3$ and X are as defined above, so obtaining a compound of formula (I) wherein A is a group

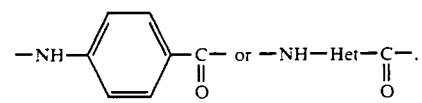

or a salt thereof.

The leaving group X in the compounds (III) and (V) may be, for example, halogen, chlorine in particular, or another displaceable group such as, for instance, 2,4,5-trichlorophenoxy, 2,4-dinitrophenoxy, succinimido-N-oxy, imidazolyl, pivaloyloxy,

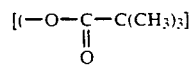

or ethyloxy formate

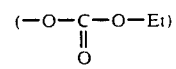

or isopropyloxy formate

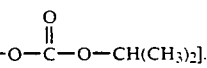

A resulting compound of formula (I) may be converted into a pharmaceutically acceptable salt if desired.

The reaction between a compound of formula (II) and a compound of formula (III) wherein X is —OH is preferably carried out at a molar ratio of (II):(III) of from 1:1 to 1:2 in an organic solvent such as, e.g., dimethylsulphoxide, hexamethylphosphotriamide, dimethylacetamide or, preferably, dimethylformamide, or their aqueous mixtures, in the presence of an organic base such as, e.g., triethylamine or diisopropyl ethylamine or an inorganic base such as, e.g., sodium bicarbonate and of a condensing agent such as, e.g., N-ethyl-N'-(3-dimethylaminopropyl) carbodiimide or, preferably, N,N'-dicyclohexylcarbodiimide. The reaction temperature may vary from about −10° C. to about 50° C. and the reaction time from about 1 to about 12 hours.

The reaction between a compound of formula (II) and a compound of formula (III), wherein X is a leaving group, e.g., 2,4,5-trichlorophenoxy or succinimido-N- oxy or imidazolyl, is usually carried out at a molar ratio of (II):(III) of from 1:1 to 1:2 in an organic solvent such as, e.g. dimethylformamide or pyridine, in the presence of an organic base, e.g. diisopropylethylamine, at a temperature from about 0° C. to about 25° C. and for about two hours to about ten hours. Similar reaction conditions may be followed when X in the compound (III) is a halogen atom.

The reaction between a compound of formula (IV) and a compound of formula (V) may be carried out in analogous conditions as those reported hereabove for the reaction between a compounds of formula (II) and a compound of formula (III) having the corresponding meanings of X.

The compounds of formula (I) prepared according to the above described procedures may be purified by conventional methods such as, e.g., silica gel or alumina column chromatography, and/or by recrystallization from organic solvents such as, e.g. lower aliphatic alcohols or dimethylformamide.

The compounds of formula (II) are known compounds or may be prepared by known methods from known compounds: see, for instance, Arcamone et al. Gazzetta Chim. Ital. 97, 1097 (1967).

The compounds of formula (IV) may be prepared following methods well known in the organic chemistry. In particular, for example, the compounds of formula (IV) wherein Z is a group

may be prepared by reacting a compound of formula (II) with p-nitrobenzoyl chloride and reducing the obtained nitro compound by known methods.

The compounds of formula (III) are known compounds or may be prepared by standard methods, for example as described in J.C.S. 1947-1032 and JACS 62, 3495 (1940). For instance, compounds of formula (III) wherein A is

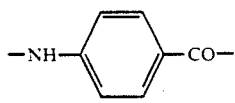

may be prepared by reaction of p-aminobenzoic acid with the activated acrylic acid derivative in a conventional way.

The compounds of the invention show cytostatic properties towards tumor cells so that they can be useful as antineoplastic agents, e.g. to inhibit the growth of various tumors, such as, for instance, carcinomas, e.g. mammary carcinoma, lung carcinoma, bladder carcinoma, colon carcinoma, ovary and endometrial tumors. Other neoplasias in which the compounds of the invention could find application are, for instance, sarcomas, e.g. soft tissue and bone sarcomas, and the hematological malignancies such as, e.g., leukemias.

The cytotoxicity of the compounds of the invention was tested, for instance, on murine L1210 leukemia cells with the following procedure. Cells were derived from in vivo tumors and established in cell culture. Cells were used until the tenth passage.

Cytotoxicity was determined by counting surviving cells after 4 hours treatment and 48 hours growth in drug-free medium.

The percentage of cell growth in the treated cultures was compared with that of controls. $ID_{50}$ values (doses inhibiting 50% of the cellular growth in respect to controls) were calculated on dose-response curves.

Thus, for example, for the compound of the invention β-(N-methyl-4-(N-methyl-4-(N-methyl-4-(N-methyl-4-(α-bromoacrylamido)pyrrole-2-carboxamido)pyrrole-2-carboxamido)pyrrole-2-carboxamido)pyrrole-2-carboxamido)propionamidine, hydrochloride, an $ID_{50}$ value of 0.003 γ/ml was found in the above test.

The compounds of the invention can be administered by the usual routes, for example, parenterally, e.g. by intravenous injection or infusion, intramuscularly, subcutaneously, topically or orally.

The dosage depends on the age, weight and conditions of the patient and on the administration route.

For example, a suitable dosage for administration to adult humans may range from about 0.05 to about 100 mg pro dose 1-4 times a day.

The pharmaceutical compositions of the invention contain a compound of formula (I) as the active substance, in association with one or more pharmaceutically acceptable excipients.

The pharmaceutical compositions of the invention are usually prepared following conventional methods and are administered in a pharmaceutically suitable form.

For instance, solutions for intravenous injection or infusion may contain as carrier, for example, sterile water or, preferably, they may be in the form of sterile aqueous isotonic saline solutions.

Suspensions or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride.

In the forms for topical application, e.g. creams, lotions or pastes for use in dermatological treatment, the active ingredient may be mixed with conventional oleaginous or emulsifying excipients.

The solid oral forms, e.g. tablets and capsules, may contain, together with the active compound, diluents, e.g., lactose, dextrose, saccharose, cellulose, corn starch and potato starch; lubricants, e.g. silica, talc, stearic acid, magnesium or calcium stearate, and/or polyethylene glycols; binding agents, e.g. starches, arabic gums, gelatin, methylcellulose, carboxymethyl cellulose, polyvinylpyrrolidone; disaggregating agents, e.g. a starch, alginic acid, alginates, sodium starch glycolate; effervescing mixtures; dyestuffs; sweeteners; wetting agents, for instance, lecithin, polysorbates, laurylsulphates; and, in general, non-toxic and pharmacologically inactive substances used in pharmaceutical formulations. Said pharmaceutical preparations may be manufactured in a known manner, for example by means of mixing, granulating, tabletting, sugar-coating, or film-coating processes.

Furthermore, according to the invention there is provided a method of treating viral infections and tumors in a patient in need of it, comprising administering to the said patient a composition of the invention.

The following examples illustrate but do not limit the invention.

The abbreviations DMF and THF stand, respectively, for dimethylformamide and tetrahydrofuran.

EXAMPLE 1

To a solution of α-bromoacrylic acid (226 mg) in dry DMF (5 ml), N,N'-dicyclohexylcarbodiimide (228 mg) was added and the resulting suspension was stirred at room temperature for 20 minutes. The mixture was added to a solution of N-deformyl Distamycin A dihydrochloride (526 mg) in DMF (10 ml) and sodium bicarbonate (84 mg).

The suspension was stirred at room temperature for 4 hours; after filtration, the solvent was evaporated in vacuum to dryness. The residue was chromatographed on silica gel with methylenechloride:methanol 80:20 as eluant, affording N-deformyl-N-(α-bromoacryloyl) Distamycin A, hydrochloride (310 mg), U.V. λmax (EtOH 95°) (ε): 242 (23772), 312 (33961) nm;

FD-M.S.: m/z 586, $M^+ +1$; 568, $M^+ -NH_3$; 505, $M^+ -HBr$;

N.M.R. (DMSO-$d_6$): δ2.62 (2H,t); 3.45 (2H,m); 3.81 (3H,s); 3.85 (6H,s); 6.20 (1H,d); 6.70 (1H,d); 6.9–7.3 (6H,m); 8.18 (1H,t); 8.6 (2H, bs); 8.96 (2H, bs); 9.88 (1H,s); 9.93 (1H,s); 10.29 (1H,s).

By analogous procedure the following compounds were obtained: N-Deformyl-N-(α-chloroacryloyl) Distamycin A, hydrochloride, U.V. λmax (EtOH 95%) (ε): 242 (23080), 310 (32972) nm;

FD-MS: m/z: 542, $M^+ +1$; 505, $M^+ -HCl$; 524, $M^+ -NH_3$;

N.M.R. (DMSO-$d_6$): δ2.65 (2H,t); 3.50 (2H,m); 3.80 (3H,s); 3.83 (3H,s); 3.84 (3H,s); 5.98 (1H,d); 6.40 (1H,d); 6.90–7.30 (6H,m); 8.20 (1H,t); 8.75 (2H,bs); 9.04 (2H,bs); 9.89 (1H,s); 9.95 (1H, s); 10.32 (1H,s).

β-(N-methyl-4-(N-methyl-4-(N-methyl-4-(N-methyl-4-(α-chloroacrylamido) pyrrole-2-carboxamido) pyrrole-2-carboxamido) pyrrole-2-carboxamido) pyrrole-2-carboxamido) propionamidine, hydrochloride.

U.V. λmax (EtOH) 95°) (ε): 244 (30.055), 314 (46098) nm;

FAB-MS: m/z: 664, $M^+ +1$; 602, $M^+ -CH_2=CCl-$;

N.M.R. (DMSO-$d_6$): δ2.62 (2H,t); 3.2–4.00 (14H,m); 5.99 (1H,d); 6.39 (1H,d); 6.90–7.30 (8H,m); 8.20 (1H,t); 8.80 (2H,bs); 9.00 (2H,bs); 9.90 (2H,s); 9.93 (1H,s); 10.30 (1H,s).

β-(N-methyl-4-(N-methyl-4-(N-methyl-4-(N-methyl-4-(α-bromoacrylamido) pyrrole-2-carboxamido) pyrrole-2-carboxamido) pyrrole-2-carboxamido)pyrrole-2-carboxamido) propionamidine, hydrochloride, U.V. λmax (EtOH 95°) (ε): 242 (29876), 314 (45224) nm;

FAB-MS: m/z: 708, $M+1$; 628, $M^+ -Br$;

N.M.R. (DMSO-$d_6$): δ2.63 (2H,t); 3.50 (2H,t); 3.80 (3H,s); 3.84 (3H,s); 3.85 (6H,s); 6.19 (1H,d); 6.69 (1H,d); 6.90–7.25 (8H,m); 8.12 (1H,t); 8.63 (2H,bs); 8.89 (2H, bs); 9.80 (1H,s); 9.83 (1H,s); 9.86 (1H,s); 10.30 (1H,s).

3-(N-methyl-4-(N-methyl-4-(N-methyl-4-(N-methyl-4-(α-chloroacrylamido) pyrrole-2-carboxamido) pyrrole-2-carboxamido) pyrrole-2-carboxamido) pyrrole-2-carboxamido) propyl-dimethylamine, U.V. λmax (EtOH 95°): 239 (29707), 313 (43738);

FAB-MS: m/z; 679, M+1; 589, $M^+ -CH_2=CCl-CO-$;

N.M.R. (DMSO-$d_6$): δ1.66 (2H,s); 2.17 (6H,s); 2.25 (2H,t); 3.20 (2H,m); 3.80 (3H,s); 3.83 (9H,s); 5.99 (1H,d); 6.37 (1H,d); 6.75–7.30 (8H,m); 8.03 (1H,t); 9.83 (1H,s); 9.90 (1H,s); 9.92 (1H,s); 10.23 (1H,s). β-(N-methyl-4-(N-methyl-4-(N-methyl-4-(N-methyl-4-(N-methyl-4-(α-bromoacrylamido) pyrrole-2-carboxamido) pyrrole-2-carboxamido) pyrrole-2-carboxamido) pyrrole-2-carboxamido)pyrrole-2-carboxamido)propionamidine, hydrochloride, U.V. λmax (EtOH 95°) (ε): 240 (34947), 312 (53018);

N.M.R. (DMSO-$d_6$): δ2.61 (2H,t); 3.48 (2H,m); 3.82 (15H,bs); 6.21 (1H,d); 6.80 (1H,d); 6.9–7.3 (10H,m); 8.19 (1H,t); 8.73 (2H,bs); 8.93 (2H, bs); 9.90 (4H,bs); 10.28 (1H,bs).

EXAMPLE 2

To a solution of (E)-β-(p-methoxybenzoyl)-β-bromoacrylic acid (428 mg), prepared according to J.O.C. 26 755 (1961), in dry D.M.F. (ml 10), cooled to 0° C., N,N'-dicyclohexylcarbodiimide (288 mg) was added and the resulting solution was stirred at 0° C. for 20 minutes.

N-Deformyl-Distamycin A-dihydrochloride (526 mg) was added, and the mixture was stirred for 30 minutes at 0° C., and then for 4 hours at room temperature. After filtration, the solvent was evaporated in vacuum to dryness, and the residue was chromatographed on silica gel with methylene chloride:methanol 80:20 as eluant affording N-deformyl-N-(E)-β-(p-methoxybenzoyl)β-bromoacryloyl)-distamycin A, hydrochloride (265 mg)

U.V. λmax (EtOH 95°) (ε): 225 (33007), 304 (32704) nm

FAB-MS: m/z 720, $M^+ +1$; 511, 389, 267

N.M.R. (DMSO-$d_6$): δ2.62 (2H,t); 3.48 (2H,m); 3.71 (3H,s); 3.74 (3H,s); 3.79 (3H,s); 3.81 (3H,s); 6.68 (1H,s); 6.75–7.20 (6H,m); 6.88 (2H,m); 7.25 (2H,m); 8.19 (1H,t); 8.54 (2H,bs); 8.93 (2H,bs); 9.88 (1H,s); 9.90 (1H,s); 10.30 (1H,s).

By analogous procedure the following compound was obtained: N-Deformyl-N-(4-(α-bromoacrylamido) benzoyl)-Distamycin A, hydrochloride, U.V. λmax (EtOH 95°) (ε): 241 (31387), 311 (48156) nm;

N.M.R. (DMSO-$d_6$): δ2.62 (2H,t); 3.45 (2H,m); 3.81 (3H,s); 3.85 (3H,s); 3.86 (3H,s); 6.34 (1H,d); 6.84 (1H,d); 6.9–7.4 (6H,m); 7.7–8.1 (4H,m); 8.20 (1H,t); 8.72 (2H,bs); 9.00 (2H,bs); 9.90 (1H,s); 9.96 (1H,s); 10.30 (1H,s); 10.56 (1H,s).

EXAMPLE 3

To a solution of acrylic acid (245 mg) in dry THF (10 ml), cooled to −10° C., triethylamine (0.47 ml) was added, and then pivaloyl chloride (0.41 ml).

The resulting suspension was stirred at −10° C. for 20 minutes, then the whole was added to a cooled solution of N-deformyl Distamycin A dihydrochloride (526 mg) in DMF (10 ml) and NaHCO$_3$ (84 mg).

The mixture was stirred for 30' at 0° C., and then for 4 hours at room temperature.

The solvent was evaporated in vacuum to dryness, and the residue was chromatographed on silica gel with methylene chloride methanol 80:20 as eluant, affording N-deformyl-N-acryloyl-Distamycin A, hydrochloride (290 mg);

U.V. λmax (EtOH 95°) (ε): 242 (23229), 308 (34164)

FD-MS: m/z 508, $M^+ +1$; 490, $M^+ -NH_3$; 437.

N.M.R. (DMSO-$d_6$): δ2.63 (2H,t); 3.50 (2H,m); 3.81 (3H,s); 3.85 (3H,s); 3.89 (3H,s); 5.66 (1H,dd); 6.19 (1H,d d); 6.46 (1H,d d); 6.90-7.30 (6H,m); 8.20 (1H,t); 8.60-9.20 (4H,b); 9.88 (1H,s); 9.90 (1H,s); 10.18 (1H,s).

By analogous procedure the following compounds were obtained: N-deformyl-N-((Z)-β-chloroacryloyl) Distamycin A, hydrochloride U.V. λmax (EtOH 95°) (ε): 243 (23254), 311 (35288) nm;

FD-MS: m/z 541, M+; 505, M+—HCl; 478;

N.M.R. (DMSO-d₆): δ2.64 (2H,t); 3.50 (2H,m); 3.80 (3H,s); 3.86 (6H,s); 6.52 (1H,d); 6.89 (1H,d); 6.9-7.3 (6H,m); 8.22 (1H,t); 8.85 (4H,b t); 9.89 (1H,s); 9.93 (1H,s); 10.28 (1H,s).

N-deformyl-N-((E)-β-chloroacryloyl) Distamycin A, hydrochloride

U.V. λmax (EtOH 95°) (ε): 241 (24584), 312 (35517) nm;

FD-MS: m/z 505, M+—HCl, 478.

N.M.R. (DMSO-d₆): δ2.64 (2H,t); 3.50 (2H,m); 3.80 (3H,s); 3.86 (6H,s); 6.70 (1H,d); 7.30 (1H,d); 6.9-7.3 (6H,m); 8.22 (1H,t); 8.85 (4H,bt); 9.89 (1H,s); 9.93 (1H,s); 10.5 (1H,s).

EXAMPLE 4

To a stirred solution of N-deformyl Distamycin A dihydrochloride (2.5 g) in water (30 ml) and dioxane (40 ml), sodium bicarbonate (2 g) was added with caution. The mixture was cooled to 5° C. and then a solution of p-nitrobenzoyl chloride (2.5 g) in dioxane (25 ml) was added in 1 hour, with vigorous stirring.

The reaction mixture was stirred for 1 hour, acidified with HCl2N to pH 4, and then evaporated to dryness in vacuum. The residue was treated with acetone (200 ml), stirred for 1 hour and filtered, to obtain N-deformyl-N-(p-nitrobenzoyl) Distamycin A hydrochloride (2.6 g).

EXAMPLE 5

The compound N-deformyl-N-(p-nitrobenzoyl) Distamycin A hydrochloride (2.6 g) was dissolved into a mixture of CH₃OH (150 ml) and 2N HCl(10 ml) and reduced over a Pd catalyst (10% on carbon) under H₂ pressure (50 p.s.i.) for 4 hours.

The catalyst was filtered and the resulting solution was concentrated in vacuum to dryness.

The residue was treated with ethanol (10 ml), stirred for 1 hour and filtered, to obtain N-deformyl-N-(p-aminobenzoyl) Distamycin A, dihydrochloride (2 g).

N.M.R. (DMSO-d₆): δ2.62 (2H,t); 3.45 (2H,m); 3.81 (3H,s); 3.85 (3H,s); 3.86 (3H,s); 6.90-7.40 (6H,m); 7.10-7.70 (4H,m); 8.20 (1H,t); 8.52 (3H,bs); 8.72 (2H,bs); 9.00 (2H,bs); 9.90 (1H,s); 9.96 (1H,s); 10.30 (1H,s).

EXAMPLE 6

Intramuscular Injection 20 mg/ml

An injectable pharmaceutical composition can be manufactured by dissolving 20 g of β-(N-methyl-4-(N-methyl-4-(N-methyl-4-(N-methyl-4-(α-bromoacrylamido)pyrrole-2-carboxamido)pyrrole-2-carboxamido)pyrrole-2-carboxamido)pyrrole-2-carboxamido)-propionamidine, hydrochloride in water for injection (1000 ml) and sealing ampoules of 1-5 ml.

We claim:

1. A compound of formula (I)

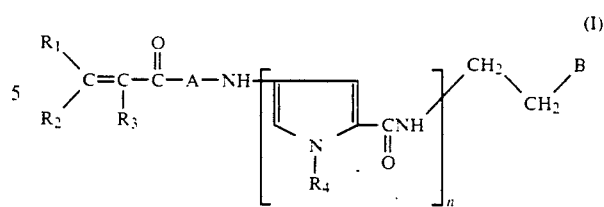

wherein n is an integer of 1 to 5;

each of R₁ and R₂, which may be the same or different, is hydrogen, halogen, —CN, —NO₂, C₁-C₄ alkyl, or a group

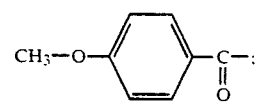

R₃ is hydrogen, halogen, —CN, or —NO₂;

each R₄ is, independently, hydrogen or C₁-C₄ alkyl;

A is a bond, a group

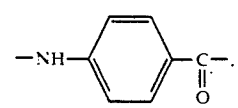

or a group —NH—Het—CO—, wherein Het is a thiophene, thiazole, pyridine, isoxazole, furane, triazole or imidazole ring; and B is a group

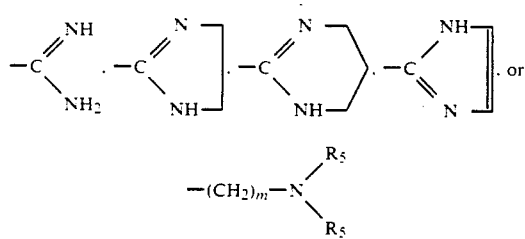

in which m is 1, 2 or 3 and each R₅ is, independently, a C₁-C₄ alkyl group; and the pharmaceutically acceptable salts thereof.

2. A compound of formula (I) according to claim 1 wherein n is 3, 4 or 5;

A is a bond or the group

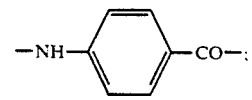

B is a group

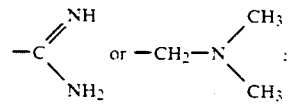

R₁ and R₂ are hydrogen;

R₃ is chlorine or bromine and R₄ is methyl;
and the salts thereof with pharmaceutically acceptable acids.

3. A compound of formula (I) according to claim 1 selected from the group consisting of:

N-deformyl-N-(α-chloroacryloyl) Distamycin A;

β-(N-methyl-4-(N-methyl-4-(N-methyl-4-(α-chloro-acrylamido) pyrrole-2-carboxamido) pyrrole-2-carboxamido) pyrrole-2-carboxamido) propionamidine;

N-deformyl-N-(α-bromoacryloyl) Distamycin A;

β-(N-methyl-4-(N-methyl-4-(N-methyl-4-(α-bromoacrylamido) pyrrole-2-carboxamido) pyrrole-2-carboxamido) pyrrole-2-carboxamido) propionamidine;

β-(N-methyl-4-(N-methyl-4-(N-methyl-4-(N-methyl-4-(N-methyl-4-(α-bromoacrylamido) pyrrole-2-carboxamido) pyrrole-2-carboxamido) pyrrole-2-carboxamido) pyrrole-2-carboxamido) propionamidine;

N-deformyl-N-(4-(α-bromoacrylamido) benzoyl)-Distamycin A;

3-(N-methyl-4-(N-methyl-4-(N-methyl-4-(N-methyl-4-(α-chloroacrylamido) pyrrole-2-carboxamido) pyrrole-2-carboxamido) pyrrole-2-carboxamido) pyrrole-2-carboxamido) propyl-dimethylamine;

and the pharmaceutically acceptable salts thereof.

4. A salt according to any one of the preceding claims wherein the salt is the hydrochloride.

5. A pharmaceutical composition containing a suitable carrier and or diluent and, as an active principle, a compound of formula (I) according to claim 1 or a pharmaceutically acceptable salt thereof.

6. A method of treating a tumor in a patient in need of such treatment, said method comprising administering an antitumor-effective amount of a compound of claim 1 to said patient.

* * * * *